(12) United States Patent
Iwase et al.

(10) Patent No.: US 8,663,163 B2
(45) Date of Patent: Mar. 4, 2014

(54) INJECTION NEEDLE AND DRUG INJECTION DEVICE

(75) Inventors: Yoichiro Iwase, Ashigarakami-gun (JP); Kazunori Koiwai, Ashigarakami-gun (JP); Tetsuo Tanaka, Ashigarakami-gun (JP); Sayaka Oomori, Ashigarakami-gun (JP); Takanori Ijitsu, Ashigarakami-gun (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 186 days.

(21) Appl. No.: 13/062,406

(22) PCT Filed: Sep. 24, 2009

(86) PCT No.: PCT/JP2009/067281
§ 371 (c)(1),
(2), (4) Date: Mar. 4, 2011

(87) PCT Pub. No.: WO2010/038879
PCT Pub. Date: Apr. 8, 2010

(65) Prior Publication Data
US 2011/0166520 A1    Jul. 7, 2011

(30) Foreign Application Priority Data

Sep. 30, 2008  (JP) ................................ 2008-255450
Nov. 18, 2008  (JP) ................................ 2008-294864

(51) Int. Cl.
*A61M 5/00* (2006.01)
*A61M 1/00* (2006.01)

(52) U.S. Cl.
USPC ......................................... 604/118; 604/115

(58) Field of Classification Search
USPC .................................................. 604/117–120
See application file for complete search history.

(56) References Cited

U.S. PATENT DOCUMENTS 6,776,776 B2 *  8/2004  Alchas et al. ................. 604/198
2002/0045858 A1  4/2002  Alchas et al.
(Continued)

FOREIGN PATENT DOCUMENTS

JP    2000-037456 A    2/2000
JP    2001-137343 A    5/2001

OTHER PUBLICATIONS

International Search Report (PCT/ISA/210) issued on Mar. 3, 2010, by Japanese Patent Office as the International Searching Authority for International Application No. PCT/JP2009/067281.

(Continued)

*Primary Examiner* — Nicholas Lucchesi
*Assistant Examiner* — Rebecca E Eisenberg
(74) *Attorney, Agent, or Firm* — Buchanan Ingersoll & Rooney PC

(57) ABSTRACT

A needle tip of a needle tube stuck in the skin is caused to be reliably positioned in the skin upper layer part and the injected drug is caused not to leak to the outside of the body. An injection needle is provided with a needle tube having a needle tip, a hub that holds the needle tube and an adjustment unit provided around the needle tube and having a needle-protruding surface through which the needle tip of the needle tube protrudes. The needle-protruding surface of the adjustment unit is formed such that the distance S from the circumferential edge to the circumferential surface of the needle tube is in the range of 0.3-1.4 mm.

13 Claims, 6 Drawing Sheets

(56) References Cited

U.S. PATENT DOCUMENTS

| | | |
|---|---|---|
| 2003/0050602 A1* | 3/2003 | Pettis et al. .................. 604/117 |
| 2007/0118077 A1 | 5/2007 | Clarke et al. |
| 2007/0185460 A1* | 8/2007 | Vedrine et al. ................ 604/240 |
| 2008/0033395 A1 | 2/2008 | Alchas |

OTHER PUBLICATIONS

R.T. Kenney et al., "Dose Sparing with Intradermal Injection of Influenza Vaccine", The New England Journal of Medicine, Nov. 25, 2004, pp. 2295-2301, vol. 351, Issue 22.

* cited by examiner

INJECTION NEEDLE AND DRUG INJECTION DEVICE

TECHNICAL FIELD

The present invention relates to an injection needle and a drug injection device that are used to inject a drug into a skin upper layer part by sticking a needle tip from the skin surface.

BACKGROUND ART

Recently, human infection of avian influenza (bird flu) has been reported, and heavy damage by human pandemic of bird flu is worried about. So, pre-pandemic vaccine that has a high possibility of being effective against bird flu is being stockpiled worldwide. Also, to administer pre-pandemic vaccine to many people, a study is being carried out on expanding the production quantity of vaccine.

Skin is composed of three parts, an epidermis, a dermis, and a portion of subcutaneous tissue. The epidermis is a layer of about 50-200 μm from the skin surface, and the dermis is a layer of about 1.5-3.5 mm continuing from the epidermis. Because influenza vaccine is generally subcutaneously or intramuscularly administered, it is administered to a lower layer part of skin or a portion deeper than that.

On the other hand, it has been reported that by administering influenza vaccine to an upper layer part of skin as a target site where many immunocompetent cells are present, even if the dosage is reduced, the same immunity acquisition ability as in subcutaneous administration or intramuscular administration can be obtained (Non-patent Document 1). Thus, by administering pre-pandemic vaccine to the skin upper layer part, the dosage can be reduced, so that there is a possibility that bird flu vaccine can be administered to more people. Note that the skin upper layer part refers to the epidermis and dermis of skin.

As the method of administering a drug to the skin upper layer part, methods using a single-needle, a multi-needle, a patch, gas, etc. have been reported. And, if stability and reliability of administration and production cost are considered, as the method of administering a drug to the skin upper layer part, the method using a single needle is most suitable. As the method of administering vaccine to the skin upper layer part using a single needle, a Mantoux method has been known from a long time ago. The Mantoux method is a method that a needle of generally 26-27 G in size having a short bevel needle tip is inserted into skin about 2-5 mm, from an oblique direction of about 10-15° relative to the skin, to administer a drug of about 100 μL.

However, the Mantoux method is difficult in manipulation and is affected by the skill of the doctor giving an injection. In particular, a child has a possibility of moving at the time of administration, so that it is difficult to administer flu vaccine with the Mantoux method. Accordingly, it is desired that a device is developed that can administer vaccine to the skin upper layer part in a simple and convenient manner.

Patent Document 1 describes an injection device for the skin upper layer part in which a limiter having a skin contacting surface is connected with a needle tube. The limiter described in Patent Document 1 is provided around a needle tube about 1-15 mm in diameter, and has a gap with the needle tube. By regulating the length (protruding length) of the needle tube protruding from the surface of the limiter contacting the skin to 0.5-3.0 mm, the drug is administered in the skin.

Also, Patent Document 2 includes description on an injection needle sticking adjustment device that prevents sticking deeper than a target depth. The injection needle sticking adjustment device disclosed in Patent Document 2 includes the one that closely contacts the circumference of a needle tube.

Patent Document 1: Japanese Laid-open Patent Application Publication No. 2001-137343
Patent Document 2: Japanese Laid-open Patent Application Publication No. 2000-037456
Non-patent Document 1: R. T. Kenney et al. New England Journal of Medicine, 351, 2295-2301 (2004)

DISCLOSURE OF THE INVENTION

Technical Problem

However, the injection device described in Patent Document 1 includes a limiter having a skin contacting surface around a needle tube, and a space of a predetermined size is provided between the limiter and the circumference of the needle tube. Because of this, if the limiter is pressed against skin, the skin is caused to bulge in the space between the limiter and the circumference of the needle tube.

The thickness of the skin upper layer part (epidermis and dermis) differs depending on administration sites, gender differences, races, and ages, however, the depth from the skin surface is in the range of about 0.5-3.0 mm. And, in Patent Document 1, it is described as that the most preferable protruding length of a needle (length protruding from the skin contacting surface of the limiter) is 1.5 mm. On the other hand, it has been reported that the skin upper layer part of a deltoid muscle, which is a common vaccine administration site, is about 1.5 mm in thickness in a case of a person having thin skin. Consequently, if the skin bulges in the space between the limiter and the circumference of the needle tube, there is a fear that the tip end of the needle tube may reach the subcutaneous tissue.

The epidermis and dermis are composed of dense fibrillar connective tissue and are harder than subcutaneous tissue, so that if the tip end of a needle tube is caused to reach subcutaneous tissue, a problem occurs that the administered drug such as vaccine, etc. moves from dermis tissue to the subcutaneous tissue and expected effects cannot be obtained.

Also, with respect to the injection needle sticking adjustment device described in Patent Document 2, if the relationship between the area of the injection needle sticking adjustment device that contacts the skin and the cross section area of the needle tube is inappropriate, there occurs a problem that the injected drug leaks to the outside of the body. If a drug is injected into the skin upper layer part, a blister is caused in the skin. On this occasion, the injection needle sticking adjustment device presses the skin and thereby a given pressure is applied to the blister, so that the injected drug is caused to leak to the outside of the body from the circumference of the needle tube.

The present invention has been made in view of the above-described circumstances, and aims to reliably position the needle tip of a needle tube stuck in the skin in the skin upper layer part and not to cause the injected drug to leak to the outside of the body.

Technical Solution

The injection needle of the present invention includes a needle tube of 26-33 G having a needle tip capable of sticking in a living body, a hub that holds the needle tube, and an adjustment unit provided around the needle tube and having a needle-protruding surface through which the needle tip of the needle tube protrudes. And, the needle-protruding surface of the adjustment unit is formed such that the distance from the circumferential edge to the circumferential surface of the needle tube is in the range of 0.3-1.4 mm.

The drug injection device of the present invention includes a needle tube of 26-33 G having a needle tip capable of being stuck in a living body, a hub that holds the needle tube, an adjustment unit having a needle-protruding surface through which the needle tip of the needle tube protrudes and fixed in close contact with the circumference of the needle tube, and a syringe that is connected with the hub. And, the needle-protruding surface of the adjustment unit is formed such that the distance from the circumferential edge to the circumferential surface of the needle tube is in the range of 0.3-1.4 mm.

Advantageous Effects

According to the injection needle and the drug injection device of the present invention, the skin that contacts the needle-protruding surface of the adjustment unit is deformed to be flat and the needle tube is stuck in the surface of the flatly deformed skin, so that the needle tip of the needle tube can be surely positioned in the skin upper layer part. Also, by setting the needle-protruding surface of the adjustment unit that contacts the skin to an appropriate size, it is possible not to cause the injected drug to leak to the outside of the body, so that the drug can be surely administered in the skin upper layer part.

BEST MODE FOR CARRYING OUT THE INVENTION

Below, exemplary embodiments of a drug injection device of the present invention are described referring to FIG. 1 through FIG. 7. Note that the same reference symbols are given to the common members in respective drawings. Further, the present invention is not limited to the embodiments described below.

1. First Embodiment

[Exemplary Configurations of an Injection Needle and a Drug Injection Device]

Figure 1:
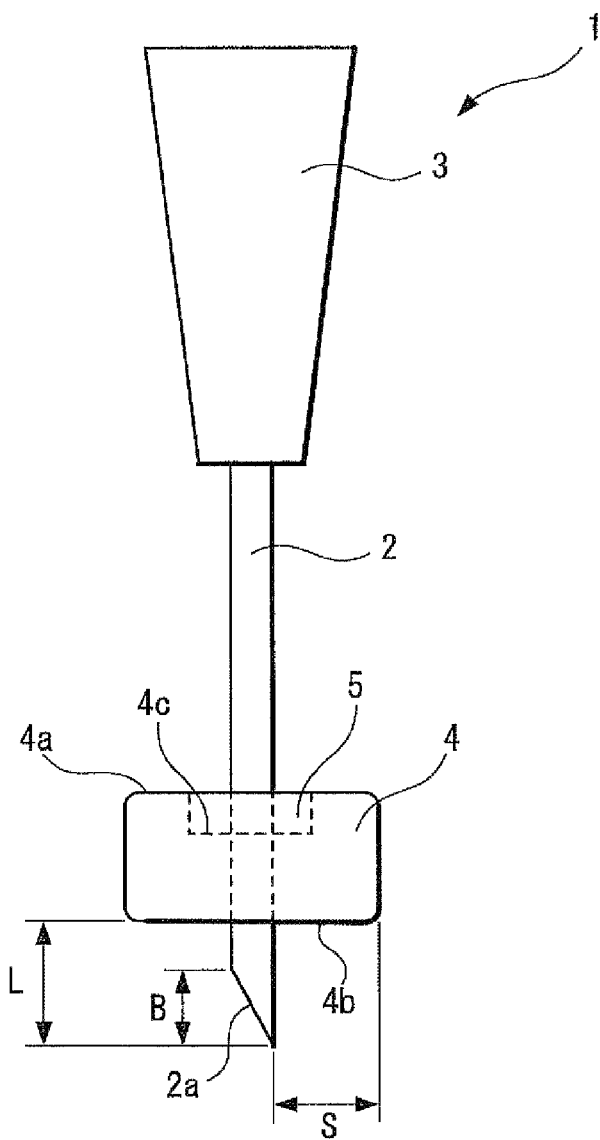
FIG. 1 is a configuration diagram illustrating an injection needle according to the first embodiment of the present invention.
Figure 2:
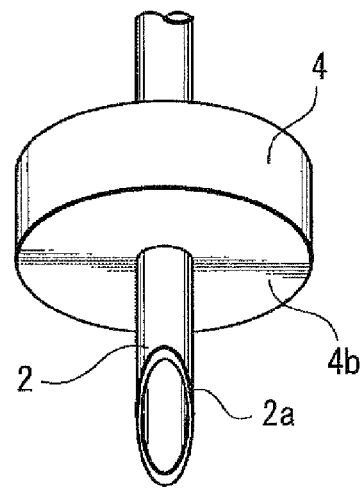
FIG. 2 is a perspective view illustrating an adjustment unit and a needle tube of the injection needle according to the first embodiment of the present invention.

First, the exterior configuration of an injection needle according to the first embodiment of the present invention is described referring to FIG. 1 and FIG. 2.

FIG. 1 is a configuration diagram illustrating the injection needle according to the first embodiment of the present invention. FIG. 2 is a perspective view illustrating an adjustment unit and a needle tube of the injection needle according to the first embodiment of the present invention.

An injection needle 1 includes a hollow needle tube 2, a hub 3 that holds the needle tube 2, and an adjustment unit 4 fixed to the needle tube 2. Further, a syringe 9 (see FIG. 6) is connected with the hub 3, thereby forming a drug injection device of the present invention.

As the needle tube 2, a needle tube of 26-33 G in size by ISO standard for medical needle tubes (ISO9626: 1991/Amd. 1:2001(E)), preferably, the one of 30-33 G, is used. At the tip end of the needle tube 2, a blade face 2a for making the needle tip acute-angled is formed. The length of the blade face 2a in the direction that the needle tube 2 extends (hereinafter, called "bevel length B") may be 1.4 mm or below, which is the thinnest thickness of the skin upper layer part (in adults) as described later, and further, may be about 0.5 mm or above, which is the bevel length when a short bevel is formed in the needle tube of 33 G. That is, the bevel length B is preferably set in the range of 0.5-1.4 mm.

Further, the bevel length B is more preferably 0.9 mm or below, which is the thinnest thickness of the skin upper layer part (in children), that is, in the range of 0.5-0.9 mm. Note that the short bevel refers to a blade face forming 18-25° relative to the longitudinal direction of the needle, which is generally used in injection needles.

As the materials of the needle tube 2, for example, stainless steel can be cited, but the materials are not limited to this, and aluminum, aluminum alloy, titanium, titanium alloy, and other metals may be used. Also, for the needle tube 2, a straight needle, and a tapered needle in which at least a portion thereof is tapered may be applied.

The tapered needle may be configured such that the base end portion that is fixed to the hub has a larger outer diameter compared with the tip end portion including the needle tip, and the middle portion thereof is tapered. Further, by providing the adjustment unit in the tapered portion, because of the existence of the slope of the tapered portion, the adjustment unit is prevented from being moved toward the base end. Thereby, even if the needle-protruding surface is strongly pressed against the skin, the length that the needle tip protrudes from the needle-protruding surface will never change, and the tapered needle can be surely stuck to a predetermined depth of the skin.

The tube hole of the needle tube 2 is communicated with the hub 3. The hub 3 holds the end portion of the needle tube 2. The hub 3 may be in any form so long as it can be connected with the syringe 9.

The syringe 9 may be the one that is filled with a drug when using the drug injection device or a pre-filled syringe filled with a drug in advance. Also, as the drug that is filled in the syringe 9, vaccine may be cited, however, it maybe those using macromolecular substances such as cytokine, etc., or hormone.

The adjustment unit 4 is formed in a cylindrical shape. The needle tube 2 penetrates through the adjustment unit 4, and the shaft center of the needle tube 2 and the shaft center of the adjustment unit 4 coincide with each other. The adjustment unit 4 is fixed in close contact with the circumferential surface of the needle tube 2. One end surface of the adjustment unit 4 forms a hub-opposing surface 4a opposing the hub 3 and the other end surface thereof forms a flat needle-protruding surface 4b from which the needle tip of the needle tube 2 protrudes.

In the hub-opposing surface 4a of the adjustment unit 4, a concave part 4c for adhesive agent is provided so as to surround the circumference of the needle tube 2. The adjustment unit 4 is fixed in close contact with the circumferential surface of the needle tube 2 by coating an adhesive agent 5 in the concave part 4c for adhesive agent in the state that the needle tube has penetrated through. As the adhesive agent 5, cyanoacrylate, epoxy resin, light curing resin, etc. may be cited, however, it may be those generated by other resin.

The needle-protruding surface 4b of the adjustment unit 4 contacts the surface of skin when the needle tube 2 is stuck in the skin upper layer part, and defines the depth that the needle tube 2 is stuck. That is, the depth that the needle tube 2 is stuck in the skin is determined by the protruding length of the needle tube 2 from the needle-protruding surface 4b (hereinafter, called "protruding length L").

The thickness of the skin upper layer part corresponds to the depth from the skin surface to the dermis layer, which is generally in the range of 0.5-3.0 mm. Therefore, the protruding length L of the needle tube 2 can be set in the range of 0.5-3.0 mm.

Further, the thickness of the skin upper layer part of a deltoid muscle, which is an influenza vaccine administration site, was measured with respect to 19 children and 31 adults. Using an ultrasonic measurement device (NP60R-UBM high-resolution echo for small animals, NEPA GENE, CO., LTD.), the skin upper layer part having high ultrasonic reflectivity was imaged and the thickness thereof was measured. Here, because the measured values showed log-normal distribution, the range of MEAN±2SD was obtained by geometrical mean. The result showed 0.9-1.6 mm with respect to children, and with respect to adults, the results were 1.4-2.6 mm in the far part, 1.4-2.5 mm in the middle part, and 1.5-2.5 mm in the near part. From the above, the thickness of the skin upper layer part of the deltoid muscle was confirmed as 0.9 mm or above in the case of children and 1.4 mm or above in the case of adults. Consequently, in an injection into the skin upper layer part of the deltoid muscle, the preferable protruding length L of the needle tube 2 can be set in the range of 0.9-1.4 mm.

Further, by setting the needle tube 2 in this manner, it becomes possible to securely position the blade face 2a in the skin upper layer part. As a result, the medicinal solution discharging outlet opened in the blade face 2a can be positioned in the skin upper layer part, regardless of its position in the blade face 2a. Note that even when the medicinal solution discharging outlet is located in the skin upper layer part, if the needle tip is stuck deeper than the skin upper layer part, the medicinal solution escapes to the outside of the skin upper layer part, which is subcutaneous tissue, from between the side faces of the needle tip end part and the incised skin. For this reason, it is important that the needle tip of the needle tube 2 and the medicinal solution discharging outlet are securely positioned in the skin upper layer part.

Note that in the case of a needle tube larger than 26 G, it is difficult to make the bevel length B 1.0 mm or smaller. Accordingly, to set the protruding length L of the needle tube 2 in the preferable range (0.9-1.4 mm), it is desirable to use a needle tube that is smaller than 26 G.

The needle-protruding surface 4b of the adjustment unit 4 is formed such that the distance S from the circumferential edge to the circumferential surface of the needle tube 2 is 1.4 mm or below, preferably in the range of 0.3-1.4 mm. This range was determined based on later-described results of experiment examples. Thereby, it can be prevented that the administered drug leaks, by the needle-protruding surface 4b depressing the skin around the needle tube 2.

As the material of the adjustment unit 4, synthetic resin (plastic), such as polycarbonate, polypropylene, polyethylene, etc., may be used, or metals such as stainless steel, aluminum, etc. may be used.

In the present embodiment, the adjustment unit 4 has been fixed to the needle tube 2 using the adhesive agent 5, however, as the injection needle of the present invention, the needle tube 2 may be fixed to the adjustment unit 4 by another method.

For example, as another method when the adjustment unit 4 is formed of metal and is fixed to the needle tube 2, swaging, welding, etc. may be cited. Also, as another method when the adjustment unit 4 is formed of synthetic resin and is fixed to the needle tube 2, fusion and integral molding (especially, insert molding) may be cited. In this case, the adjustment unit 4 may be extended in the base end direction and integrated with the hub 3. Thereby, it becomes easier to position the adjustment unit 4.

[Method of Using Drug Injection Device]

Figure 3:
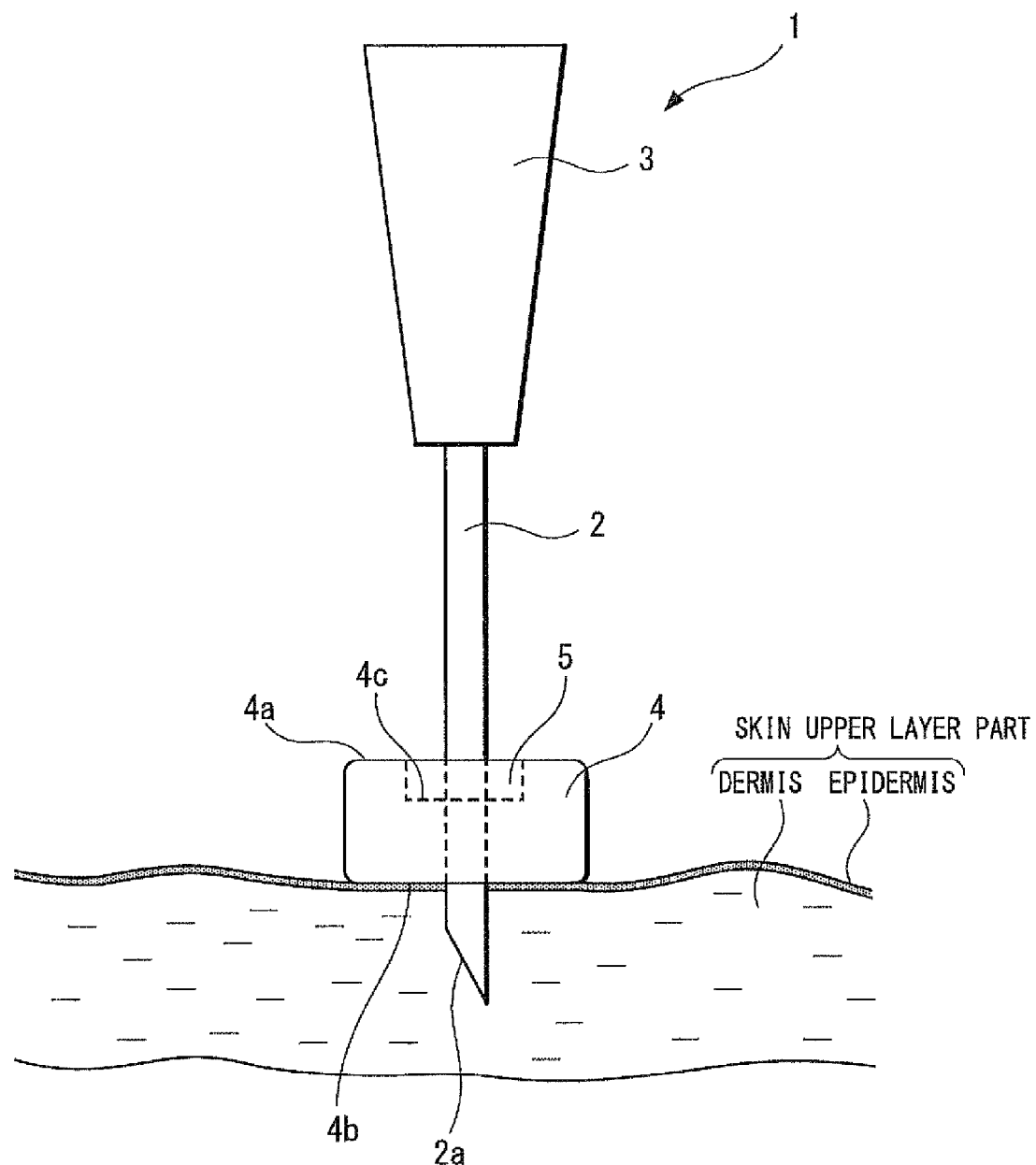
FIG. 3 is an explanatory diagram illustrating a state that a needle tube of a drug injection device using the injection needle according to the first embodiment of the present invention has been stuck in the skin.

Next, a method of using a drug injection device to which the injection needle 1 has been applied is described referring to FIG. 3.

FIG. 3 is an explanatory diagram illustrating a state that the needle tube 2 of the injection needle 1 of the drug injection device has been stuck in the skin.

First, the needle tip of the needle tube 2 is caused to face the skin into which the needle tube is stuck. Next, the injection needle 1 is moved substantially perpendicularly relative to the skin, and the needle tube 2 is stuck in the skin. At this time, the needle tube 2 is stuck in the skin until the needle-protruding surface 4b of the adjustment unit 4 contacts the skin. Thereby, the skin contacting the needle-protruding surface 4b of the adjustment unit 4 can be deformed flat, and the needle tube 2 can be stuck in the skin only by the protruding length L.

Because the protruding length L is set in the range of 0.5-3.0 mm, the needle tip of the needle tube 2 is securely positioned in the skin upper layer part. Thereafter, a drug is injected into the skin upper layer part by a syringe (not shown) connected with the hub 3.

The adjustment unit 4 of the injection needle 1 is fixed in close contact with the circumference of the needle tube 2, and it is configured such that a gap is not formed between the portion of the needle tube 2 penetrating through the adjustment unit 4 and the adjustment unit 4. Consequently, if the needle-protruding surface 4b of the adjustment unit 4 is brought into contact with skin, the skin around the needle tube 2 can be deformed flat. As a result, the needle tube 2 can be stuck in the skin only by the protruding length L, and the needle tip of the needle tube 2 can be surely positioned in the skin upper layer part.

Also, because the needle-protruding surface 4b of the adjustment unit 4 has been set in an appropriate size, the injected drug can be prevented from leaking to the outside of the body, and the drug can be securely injected into the skin upper layer part.

[Examples of Experiment]

Next, explanation is made with respect to examples of an experiment of injecting a drug while varying the size of the needle-protruding surface 4b of the adjustment surface 4.

In the drug injection device used in the experiment, a hollow needle of 30 G (outer diameter=about 0.3 mm) was employed as the needle tube. The adjustment unit was formed by molding resin in a cylindrical shape having a hole in the center. The protruding length of the needle tube inserted into the hole was set to 1.5 mm. The adjustment unit was fixed to the needle tube by injecting an adhesive agent into a gap between the adjustment unit and the needle tube from the base end part side of the needle tube. And, the diameter of the adjustment unit was set to 15 mm, 12 mm, 9.0 mm, 6.0 mm, 5.5 mm, 5.0 mm, 4.5 mm, 4.0 mm, 3.0 mm, 2.0 mm, and 0.9 mm.

As the drug for administration, a radiographic contrast agent, Oypalomin 370 (trademark) (100 μL, Fuji Pharma Co., Ltd.), was diluted by a physiological saline solution to about 25%, and the dosage was set to about 100 μL. As the object that the drug is to be administered, a piece of fresh meat from the epidermis to the muscle layer removed from a miniature pig weighing about 30 kg was used. With respect to the pushing force of the adjustment unit 4 against the epidermis at the time of administration, the piece of the miniature pig meat was placed on a weighing machine and pushed by the administrator immediately before administration, and the pushing force thereof was measured. The pushing force measured by the weighing machine was in the range of 3-15 N.

The evaluation of the experiment was carried out with respect to leakage of the drug and distribution of the drug. Leakage of the drug was evaluated by visual observation. Drug distribution was evaluated by confirming it using a radiographic contrast device (Shimadzu DIGITEX α plus of Shimadzu Corporation). The skin upper layer part to which the drug is administered has lower permeability than the underlying subcutaneous tissue, so that when subjected to radiographic imaging, it is imaged more blackly than the subcutaneous tissue. Also, the administered drug is imaged more blackly than the skin upper layer part. Accordingly, by carrying out radiographic imaging, whether or not the drug is distributed in the skin upper layer part can be confirmed.

The experiment result is shown in Table 1.

TABLE 1

Evaluation result on drug leakage when size of needle-protruding surface has been varied

| A/mm | | | | | | | | | | | | |
|---|---|---|---|---|---|---|---|---|---|---|---|---|
| | 15 | 12 | 9.0 | 6.0 | 6.0 | 5.5 | 5.0 | 4.5 | 4.0 | 3.0 | 2.0 | 0.9 |
| | | | | | | B/mm | | | | | | |
| | 7.4 | 5.9 | 4.4 | 2.9 | 2.9 | 2.6 | 2.4 | 2.1 | 1.9 | 1.4 | 0.9 | 0.3 |
| 1st round | x | x | x | o | Δ | Δ | — | Δ | Δ | o | o | o |
| 2nd round | x | x | x | x | Δ | Δ | Δ | Δ | Δ | o | o | o |
| 3rd round | — | — | x | Δ | Δ | Δ | Δ | Δ | Δ | — | o | — |

A: adjustment member/mm
B: distance from circumferential edge of needle-protruding surface to circumferential surface of needle tube/mm
x: needle tube was not stuck in the skin and leakage was caused
Δ: needle tube was stuck, however leakage was caused
o: leakage was not caused
—: experiment was not carried out Table 1 shows the evaluation with respect to leakage of the drug when the size of the needle protruding surface 4b has been varied. As shown in Table 1, in the range of 2.9-7.4 mm of the distance from the circumferential edge of the needle-protruding surface to the circumferential surface of the needle tube (the diameter of the adjustment unit is 6.0-15 mm), it was visually confirmed that the drug had leaked to the outside of the body. Further, confirming the image of radiographic imaging, the contrast agent was not distributed in the skin upper layer part. Accordingly, it is considered that in the range of 2.9-7.4 mm of the distance from the circumferential edge of the needle-protruding surface to the circumferential surface of the needle tube, because the needle tube will not stick in the skin, the drug leaked.

In the range of 1.9-2.6 mm of the distance from the circumferential edge of the needle-protruding surface to the circumferential surface of the needle tube (the diameter of the adjustment unit is 4.0-5.5 mm), it was visually confirmed that the leakage amount of the drug had decreased. Further, confirming the image of radiographic imaging, the drug was distributed in the skin upper layer part. Based on this, it is understood that the needle tube was stuck in the skin and the drug was administered to the skin upper layer part.

However, it is considered that by thrusting the skin around the needle tube with the needle-protruding surface of the adjustment unit, pressure was placed on a blister that is formed by administering the drug to the skin upper layer part and thereby the administered drug leaked.

In the range of 0.3-1.4 mm of the distance from the circumferential edge of the needle-protruding surface to the circumferential surface of the needle tube (the diameter of the adjustment unit is 0.9-3.0 mm), leakage of the drug was not visually confirmed. Further, confirming the image of radiographic imaging, the drug was distributed in the skin upper layer part. It is considered that this is because the needle-protruding surface of the adjustment unit is sufficiently smaller than a blister that is formed by administering a drug to the skin upper layer part and does not prevent formation of the blister.

That is, it is believed that the adjustment unit in which the distance from the circumferential edge of the needle-protruding surface to the circumferential surface of the needle tube is in the range of 0.3-1.4 mm controls the depth that the needle tube is stuck in the skin, and does not prevent formation of a blister. Accordingly, the drug injection device using an injection needle having an adjustment unit in which the distance from the circumferential edge of the needle-protruding surface to the circumferential surface of the needle tube is in the range of 0.3-1.4 mm can surely distribute a drug in the skin upper layer part without causing leakage of the drug to the outside of the body. Note that if the needle-protruding surface stops by contacting the skin and thereby the depth that the needle tube is inserted into the skin can be regulated, the distance from the circumferential edge of the needle-protruding surface to the circumferential surface of the needle tube can be set smaller than 0.3 mm.

When the distance from the circumferential edge of the needle-protruding surface to the circumferential surface of the needle tube is 1.4 mm (the diameter of the adjustment unit is 3.0 mm), the area of the needle-protruding surface is $\pi(1.5)^2$. On the other hand, the area of the cross section of a needle tube composed of a hollow needle of 30 G (outer diameter=about 0.3 mm) is $\pi(0.3)^2$. That is, such an experiment result was obtained that if the area of a needle-protruding surface in a drug injection device is about 25 times or smaller of the cross section of a needle tube, the drug will not leak to the outside of the body and the drug can be surely distributed in the skin upper layer part.

Also, in the range of 1.9-2.6 mm of the distance from the circumferential edge of the needle-protruding surface to the circumferential surface of the needle tube (the diameter of the adjustment unit is 4.0-5.5 mm), the drug can be distributed in the skin upper layer part. When the distance from the circumferential edge of the needle-protruding surface to the circumferential surface of the needle tube is 2.6 mm (the diameter of the adjustment unit is 5.5 mm), the area of the needle-protruding surface is $\pi(2.75)^2$. That is, such an experiment result was obtained that if the area of the needle-protruding surface in a drug injection device is about 84 times or below of the cross section of a needle tube, the drug can be distributed in the skin upper layer part.

2. Second Embodiment

[Exemplary Configurations of an Injection Needle and a Drug Injection Device]

Figure 4:
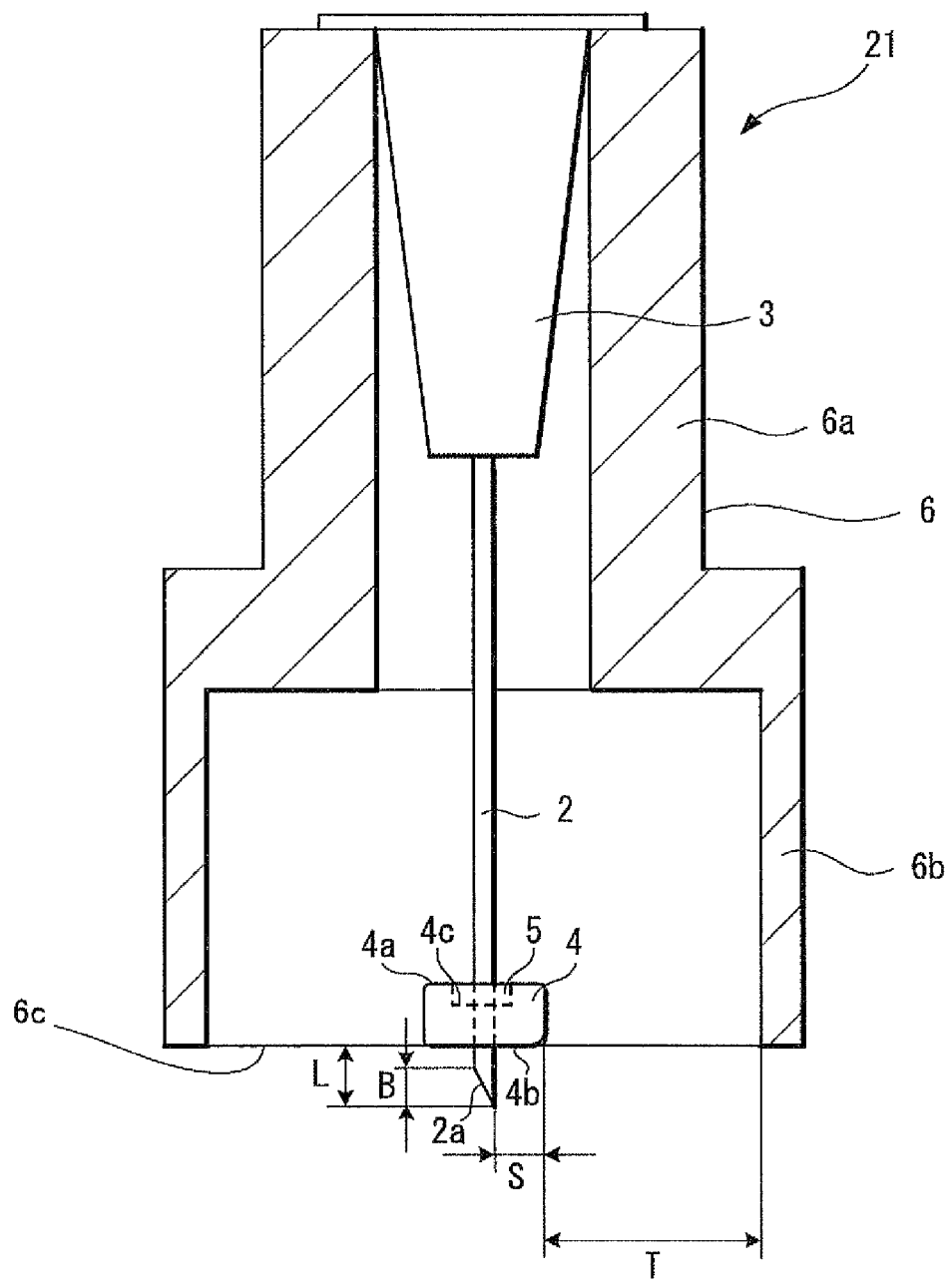
FIG. 4 is a configuration diagram illustrating an injection needle according to the second embodiment of the present invention.
Figure 5:
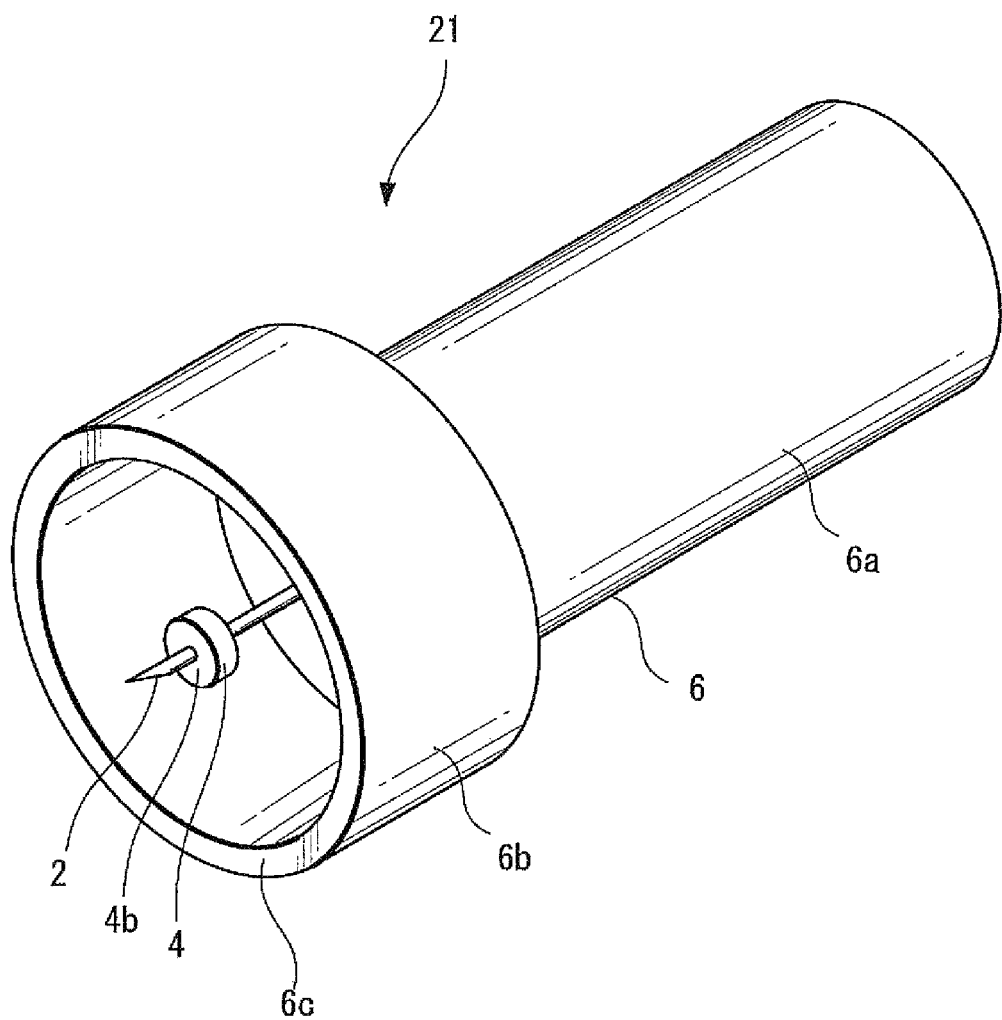
FIG. 5 is a perspective view illustrating the injection needle according to the second embodiment of the present invention.

Next, the exterior configuration of an injection needle according to the second embodiment of the present invention is described referring to FIG. 4 and FIG. 5.

FIG. 4 is a configuration diagram illustrating the injection needle according to the second embodiment. FIG. 5 is a perspective view illustrating the injection needle according to the second embodiment.

Incidentally, in the technology described in Patent Document 2, if the size of an injection needle sticking adjustment device that is in close contact with the circumference of a needle tube is too small, the needle tube is easy to waggle, and it was difficult to stick the needle tube straight to the skin. Therefore, with the technology described in Patent Document 2, there has been a problem that because of waggling of the needle tube, stable administration of a drug is not possible and thereby leakage of the drug is caused, and the needle tip of a needle tube stuck in the skin cannot be securely positioned in the skin upper layer part.

Note that it is conceivable to enlarge the size of an injection needle sticking adjustment device to stabilize a needle tube. However, if the size of the injection needle sticking adjustment device is enlarged, a trouble occurs that formation of a blister is prevented by thrusting the skin with the injection needle sticking adjustment device and the injected drug leaks from the circumference of the needle tube to the outside of the body.

Consequently, in an injection needle 21 and a drug injection device according to the second embodiment, in view of the above-described problems, it has been configured such that waggling of the needle tube is prevented so that stable administration of a drug can be carried out, and the injected drug can be prevented from leaking to the outside of the body.

The injection needle 21 includes a hollow needle tube 2, a hub 3 that holds the needle tube 2, an adjustment unit 4 fixed to the needle tube 2, and a stabilizer unit 6. Note that by connecting a syringe 9 shown by a broken line with the hub 3, a drug injection device of the present invention is constituted (see FIG. 6). The needle tube 2, the hub 3, and the adjustment unit 4 are common members with the injection needle 1 according to the first embodiment, so that description thereof is omitted.

The stabilizer unit 6 has a shape that two cylinders different in diameter are continuous in the axial direction. In the cylindrical hole of the stabilizer unit 6, arranged are the needle tube 2, the hub 3, and the adjustment unit 4. Further, the stabilizer unit 6 includes a fixing part 6a that is fixed to the hub 3, and a contact part 6b that covers the circumference of the needle tube 2 and the adjustment unit 4. The fixing part 6a is fixed to the hub 3 by a fixing means such as an adhesive agent, etc. At one end side in the axial direction of the fixing part 6a, the contact part 6b is continuously provided.

The contact part 6b is arranged, by fixing the fixing part 6a to the hub 3, so as to cover the circumference of the needle tube 2 and the adjustment unit 4. The inner diameter of the contact part 6b is set so as to be larger than the inner diameter of the fixing part 6a. Further, an end face 6c at one end side in the axial direction of the contact part 6b is positioned on substantially the same plane as the needle-protruding surface 4b of the adjustment unit 4. And, the needle tube 2 is orthogonal to a plane formed by the end face 6c of the stabilizer unit 6 and the needle-protruding surface 4b of the adjustment unit 4.

Accordingly, when the needle tube 2 is stuck in a living body (see FIG. 6), the needle-protruding surface 4b of the adjustment unit 4 contacts the skin surface and the end face 6c of the stabilizer unit 6 also contacts the skin surface. Thereby, the needle tube 2 can be supported by the stabilizer unit 6 substantially perpendicularly to the skin. As a result, it can be prevented that the needle tube 2 waggles, and it enables that the needle tube 2 is stuck straight to the skin.

Further, the inner diameter of the contact part 6b of the stabilizer unit 6 is set such that a distance T from the inner wall surface to the outer circumferential surface of the adjustment unit 4 is in the range of 4-15 mm. This range was determined based on results of experiment examples described later.

As the material of the stabilizer unit 6, similarly to the adjustment unit 4, synthetic resin (plastic), such as polycarbonate, polypropylene, polyethylene, etc., may be used, and also, metals such as stainless steel, aluminum, etc. may be used.

Note that the shape of the stabilizer unit 6 is not limited to a circular tube shape, and may be formed, for example, in a rectangular tube shape, such as a quadrangular prism, a hexagonal prism, etc., having a tube hole in the center. Also, a cut may be provided in the contact part 6b, and further, the stabilizer unit may be formed such that the diameters of the fixing part 6a and the contact part 6b are the same.

Further, although the example that the stabilizer unit 6 is fixed to the hub 3 has been explained, the stabilizer unit 6 may be fixed to a syringe that constitutes the drug injection device. Also, in the present embodiment, the stabilizer unit 6 has been fixed to the hub 3 using an adhesive agent, however, as the injection needle of the present invention, the stabilizer unit 6 may be fixed to the hub 3 by another method. For example, as another method when the stabilizer unit 6 is formed of metal and is fixed to the hub 3, swaging, welding, etc. may be given. Further, as another method when the stabilizer unit 6 is formed of synthetic resin and is fixed to the hub 3, fusion and integral molding (especially, insert molding) may be cited.

[Method of Using Drug Injection Device]

Figure 6:
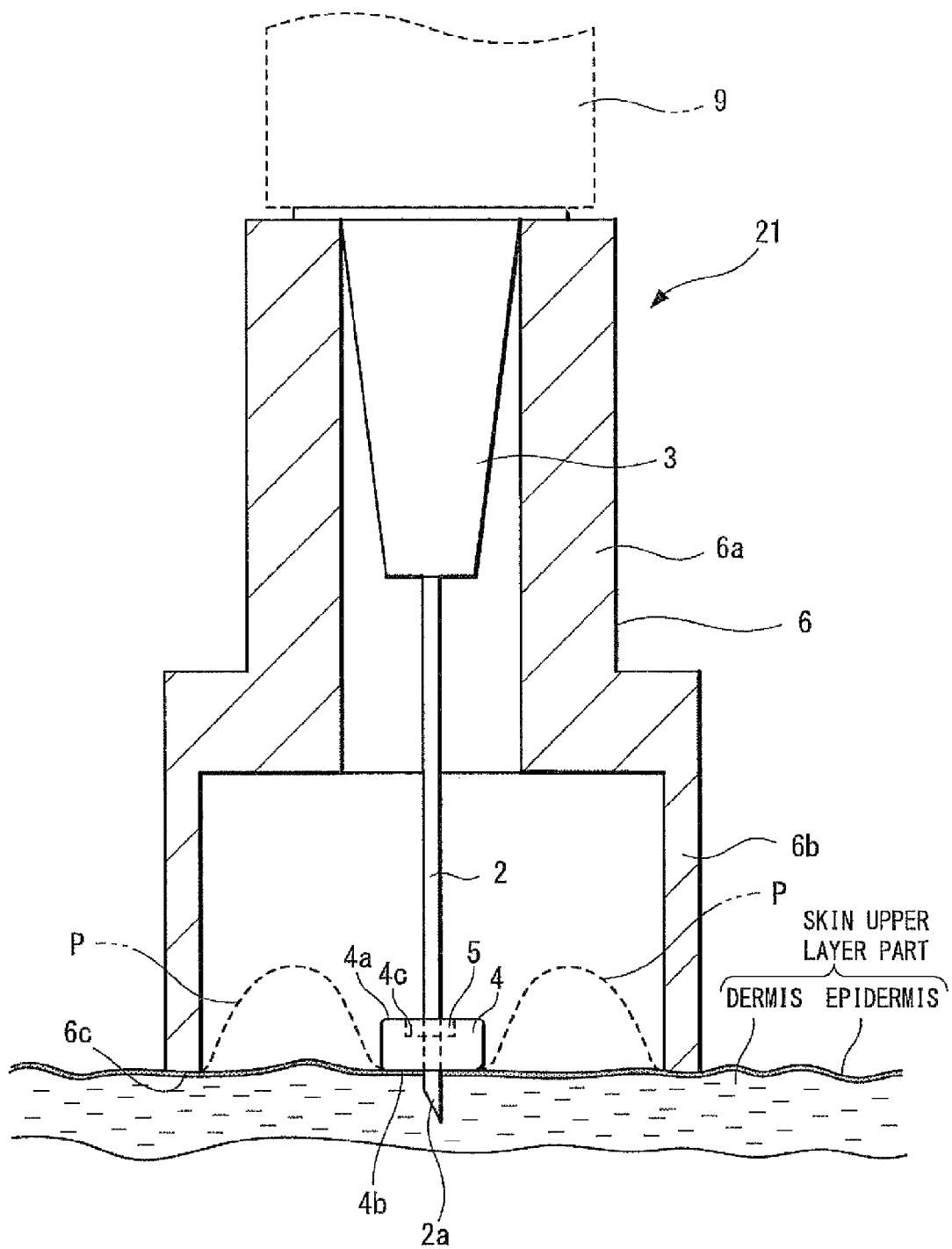
FIG. 6 is an explanatory diagram illustrating a state that a needle tube of a drug injection device using the injection needle according to the second embodiment of the present invention has been stuck in the skin.

Next, a method of using a drug injection device to which the injection needle 21 has been applied is described referring to FIG. 6.

FIG. 6 is an explanatory diagram illustrating a state that the needle tube 2 of the injection needle 21 of the drug injection device has been stuck in the skin.

First, the needle tip of the needle tube 2 is caused to face the skin into which the needle tube 2 is stuck. Next, the injection needle 21 is moved substantially perpendicularly relative to the skin, and the needle tube 2 is stuck in the skin. At this time, the needle tube 2 is stuck in the skin until the needle-protruding surface 4b of the adjustment unit 4 and the end face 6c of the stabilizer unit 6 are brought into contact the skin. Thereby, the skin contacting the needle-protruding surface 4b of the adjustment unit 4 can be deformed flat, and the needle tube 2 can be suck in the skin only by the protruding length L. Also, by causing the stabilizer unit 6 to contact the skin, the needle tube 2 is caused to stabilize, and thereby the needle tube 2 can be stuck straight to the skin. Further, because it is possible to prevent waggling that is caused in the needle tube 2, stable administration of a drug can be carried out.

When using a needle with a very short protruding length, for example about 0.5 mm, there is a case that the needle will not stick in the skin even if the needle tip is brought into contact with the skin. However, when the stabilizer unit 6 is thrust against the skin and the skin is pressed down perpendicularly, the skin inside the stabilizer unit 6 is strained to be in a tensioned state. Consequently, the skin becomes hard to flee from the needle tip of the needle tube 2, so that there is also such an effect that the stabilizer unit 6 makes it easier for the needle tip to stick in the skin.

Thereafter, a drug is injected into the skin upper layer part using a syringe (not shown) connected with the hub 3. At this time, because the outer diameter of the needle-protruding surface 4b of the adjustment unit 4 and the inner diameter of the stabilizer unit 6 are set to appropriate sizes, it is possible to prevent the injected drug from leaking to the outside of the body, and the drug can be surely administered in the skin upper layer part. As a result, a blister P shown by a broken line is formed between the inner wall surface of the contact part 6b of the stabilizer unit 6 and the outer circumferential surface of the adjustment unit 4.

Thus, according to the injection needle 21 of the second embodiment and a drug injection device using the injection needle 21, when sticking the needle tube 2 in a living body, the stabilizer unit 6 is brought into contact with the skin, so that waggling of the needle tube 2 can be prevented, and the needle tube 2 can be stuck straight relative to the skin. Thereby, the needle tip of the needle tube 2 can be reliably positioned in the skin upper layer part, and stable administration of a drug can be carried out. Further, by setting the needle-protruding surface 4b of the adjustment unit 4 that contacts the skin in an appropriate size, it is possible to prevent the injected drug from leaking to the outside of the body.

[Examples of Experiment]

Next, explanation is made with respect to examples of an experiment of administering a drug while varying the size of the internal diameter of the stabilizer unit.

In the drug injection device used in the experiment, a hollow needle of 30 G (outer diameter=about 0.3 mm) was employed as the needle tube. The adjustment unit was formed by molding resin in a cylindrical shape having a hole in the center. The protruding length of the needle tube inserted into the hole was set to 1.5 mm. The adjustment unit was fixed to the needle tube by injecting an adhesive agent into a gap between the adjustment unit and the needle tube from the base end part side of the needle tube. Note that the diameter of the adjustment unit 4 was set to 0.9 mm. And, the internal diameter of the contact part 6b of the stabilizer unit 6 was set to 13 mm, 11 mm, 9 mm, 7 mm, 5 mm, and 3 mm.

As the drug for administration, a radiographic contrast agent, Oypalomin 370 (trademark) (100 mL, Fuji Pharma Co., Ltd.), was diluted by a physiological saline solution to about 25%, and the dosage was set to about 100 μL. As the object that the drug is to be administered, swine having a property that is relatively close to that of human dermal tissue was selected, and a piece of fresh meat from the epidermis to the muscle layer removed from a miniature pig weighing about 30 kg was used. With respect to the pushing force of the adjustment unit against the epidermis at the time of administering, the piece of the miniature pig meat was placed on a weighing machine and pushed immediately before administration by the administrator, and the pushing force thereof was measured. The pushing force measured by the weighing machine was in the range of 3-15 N.

The evaluation of the experiment was carried out with respect to leakage of the drug and distribution of the drug. Leakage of the drug was evaluated by visual observation. And, drug distribution was evaluated by confirming it using a radiographic contrast device (Shimadzu DIGITEX α plus of Shimadzu Corporation). The skin upper layer part to which the drug is administered has lower permeability than the underlying subcutaneous tissue, so that when subjected to radiographic imaging, it is imaged more blackly than the subcutaneous tissue. Also, the drug that is administered is imaged more blackly than the skin upper layer part. Accordingly, by carrying out radiographic imaging, whether or not the drug is distributed in the skin upper layer part can be confirmed.

The experiment result is shown in Table 2.

TABLE 2

| | A/mm | | | | | |
|---|---|---|---|---|---|---|
| | 13 | 11 | 9 | 7 | 5 | 3 |
| | B/mm | | | | | |
| | 6 | 5 | 4 | 3 | 2 | 1 |
| 1st round | | | | | | |
| Leakage | ○ | ○ | ○ | x | x | x |
| Blister-Formation | not prevented | slightly prevented | slightly prevented | prevented | prevented | prevented |
| 2nd round | | | | | | |
| Leakage | — | ○ | ○ | x | x | x |
| Blister-formation | — | slightly prevented | slightly prevented | prevented | prevented | prevented |

A: internal diameter of stabilizer unit/mm
B: distance from inner wall surface of stabilizer unit to outer circumferential surface of adjustment unit/mm
○: no leakage
x: leakage is caused Table 2 shows the evaluation with respect to leakage of the drug and formation a blister when the size of the internal diameter of the stabilizer unit 6 has been varied. As shown in Table 2, in the range of 1.0-3.0 mm of the distance from the inner wall surface of the contact part 6b of the stabilizer unit 6 to the outer circumferential surface of the adjustment unit 4 (the internal diameter of the stabilizer unit 6 is 3.0-7.0 mm), it was visually confirmed that the drug had leaked to the outside of the body. Further, confirming the image of radiographic imaging, the contrast agent was not distributed in the skin upper layer part. Accordingly, it is considered that in the range of 1-3 mm of the distance from the inner wall surface of the stabilizer unit 6 to the outer circumferential surface of the adjustment unit 4, the drug leaked because the internal diameter of the stabilizer unit 6 was smaller than the diameter of the blister P and thereby the contact part 6b of the stabilizer unit 6 prevented blister formation.

On the other hand, in the range of 4-6 mm of the distance from the inner wall surface of the stabilizer unit 6 to the outer circumferential surface of the adjustment unit 4 (the internal diameter of the contact part 6b of the stabilizer unit 6 is 9-13 mm), leakage of the drug could not be visually confirmed. Further, confirming the image of radiographic imaging, the drug was distributed in the skin upper layer part. From this, it is understood that the needle tube 2 was stuck in the skin and the drug was administered in the skin upper layer part. It is believed that this is because the inner diameter of the stabilizer unit 6 is equal to or larger than the diameter of the blister P and consequently the stabilizer unit 6 did not prevent formation of a blister.

Accordingly, in the range of 4-6 mm of the distance T from the inner wall surface of the stabilizer unit 6 (contact part 6b) to the outer circumferential surface of the adjustment unit 4, the needle sticking length can be reliably defined by the adjustment unit 4. Further, it is possible to make the outer diameter of the adjustment unit 4 small for preventing leakage and to eliminate resultant waggling of the needle tube by the stabilizer unit 6. Note that if the distance T from the inner wall surface of the stabilizer unit 6 to the outer circumferential surface of the adjustment 4 is 4 mm or above, it has no particular upper limit. However, if the distance T is too large, when administering to a slender arm like those of small children, conversely it becomes impossible to carry out stable administration. For this reason, when slender arms of children are considered, the distance T from the inner wall surface of the stabilizer unit 6 (contact part 6*b*) to the outer circumferential surface of the adjustment unit 4 can be defined to 15 mm as the maximum.

3. Third Embodiment

[Configuration Examples of an Injection Needle and a Drug Injection Device]

Figure 7:
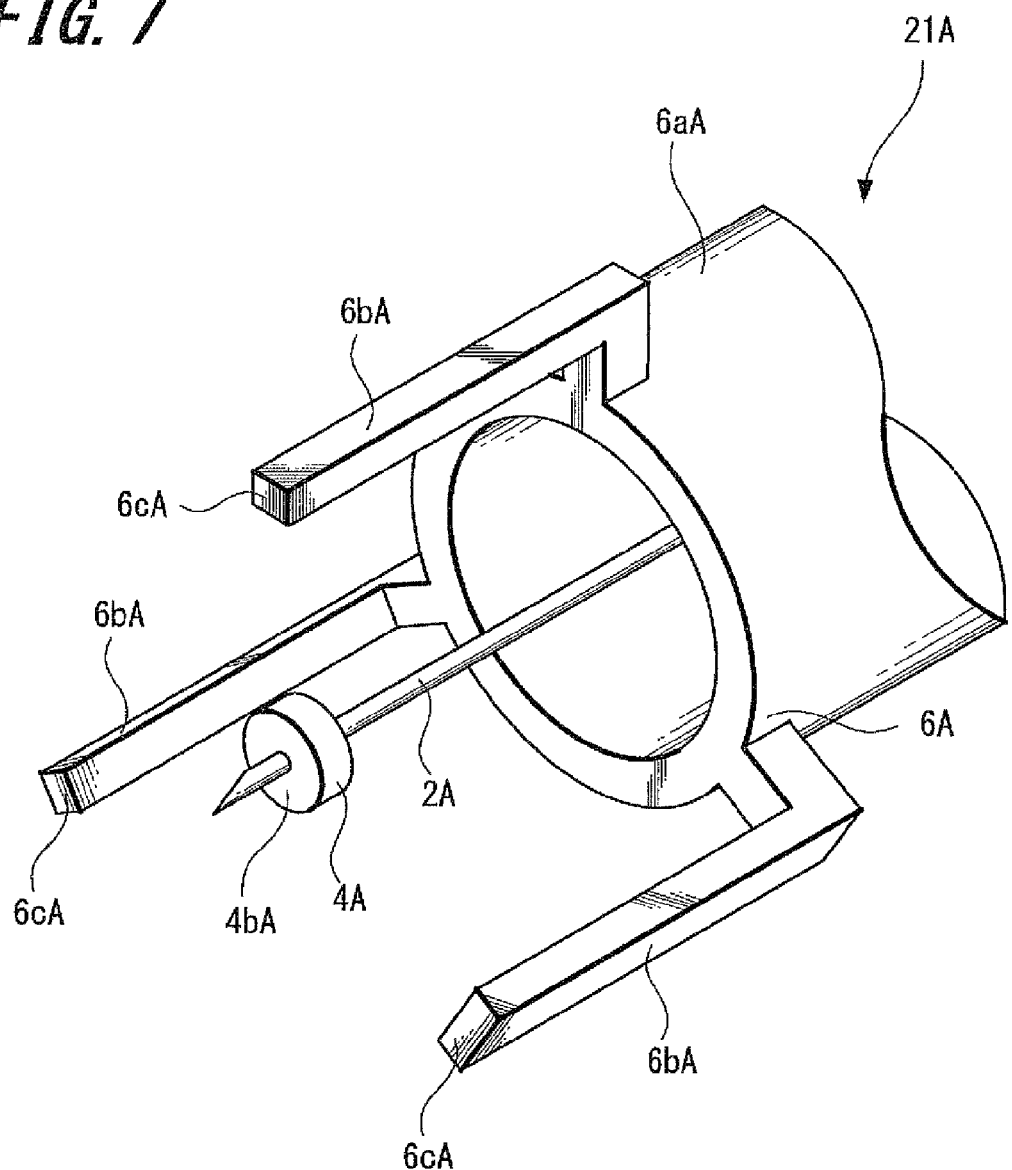
FIG. 7 is a perspective view illustrating an injection needle according to the third embodiment of the present invention.

Next, explanation is made with respect to an example of an injection needle according to the third embodiment of the present invention referring to FIG. 7.

FIG. 7 is a perspective view illustrating the injection needle according to the third embodiment.

An injection needle 21A according to the third embodiment is the one obtained by changing the shape of the stabilizer unit 6 of the injection needle 21 according to the second embodiment.

As illustrated in FIG. 7, the injection needle 21A includes a hollow needle tube 2, a hub that holds the needle tube 2, which is not shown in the drawing, an adjustment unit 4 fixed to the needle tube 2, and a stabilizer unit 6A. The needle tube 2, the hub, and the adjustment unit 4 are common members with the injection needle 1 in the first embodiment, so that description thereof is omitted.

The stabilizer unit 6A is constituted by a substantially cylindrical fixing part 6*a*A and three contact parts 6*b*A. The three contact parts 6*b*A are leg-like members protruding from a side surface of the fixing part 6*a*A to one side in the axial direction of the stabilizer unit 6A. These three contact parts 6*b*A are arranged at substantially equal angular intervals (for example, 120° intervals). Also, a plane defined by end faces 6*c*A at one end side in the axial direction of the three contact parts 6*b*A is positioned on substantially the same plane as the needle-protruding surface 4*b* of the adjustment unit 4.

Also, when the needle tube 2 is stuck in a living body, the three end faces 6*c*A of the stabilizer unit 6A are brought into contact with the skin. Thus, by supporting the injection needle 21A in a well-balanced manner by the three contact parts 6*b*A of the stabilizer unit 6A, it is enabled to prevent waggling caused in the needle tube 2.

Note that in the third embodiment, description has been made with respect to an example that three contact parts are provided, however, it is not limited to this. It is needless to say that for example, four or more contact parts may be provided.

With the injection needle 21A having such a configuration also, it is possible to obtain functions and effects similar to those of the injection needle 21 according to the above-described second embodiment.

Note that in the case of the stabilizer unit 6A according to the third embodiment, by making the intervals of the three contact parts 6*b*A larger, the pressure applied to the blister from the three contact parts 6*b*A of the stabilizer unit 6A can be decreased. As a result, according to the stabilizer unit 6A according to the third embodiment, it is believed that the distance from the inner wall surface to the outer circumferential surface of the adjustment unit 4 can be made shorter than the stabilizer unit 6 in a cylindrical shape.

Description has been made above with respect to the embodiments of the injection needle and the drug injection device of the present invention, including functions and effects thereof. However, the injection needle and the drug injection device of the present invention are not limited to the above-described embodiments, and various modifications thereof may be possible within the gist of the invention described in the scope of claims.

EXPLANATION OF REFERENCE SYMBOLS

1, 21, 21A; injection needle
2; needle tube
2*a;* blade face
3; hub
4; adjustment unit
4*a;* hub-opposing surface
4*b;* needle-protruding surface
4*c;* concave part for adhesive agent
5; adhesive agent
6, 6A; stabilizer unit
6*a,* 6*a*A; fixing part
6*b,* 6*b*A; contact part
6*c,* 6*c*A; end face
9; syringe
B; bevel length
L; protruding length
S; distance from circumferential edge of needle-protruding surface to circumferential surface of needle tube
T; distance from inner wall surface of stabilizer unit to the outer circumferential surface of adjustment unit 4
P; blister

The invention claimed is:

1. An injection needle comprising:
    a needle tube of 26-33 G having a needle tip capable of sticking in a living body, the needle tip having a bevel with a bevel length defined by a blade face in the needle tube extending direction;
    a hub that holds the needle tube; and
    an adjustment unit provided around the needle tube and having a needle-protruding surface from which the needle tip of the needle tube protrudes, wherein the adjustment unit is formed such that a shortest distance from a circumferential edge of the needle-protruding surface to a circumferential surface of the needle tube is in a range of 0.5-1.4 mm;
    wherein a protruding length of the needle tube from the needle protruding surface is 0.9-1.4 mm, and the bevel length is 0.5-0.9 mm.

2. The injection needle described in claim 1, further comprising:
    a stabilizer unit provided around the needle tube with a predetermined interval from the adjustment unit and having an end face that contacts a skin when sticking the needle tube in a living body.

3. The injection needle described in claim 2, wherein the stabilizer unit is formed in a cylindrical shape covering a circumference of the needle tube and the adjustment unit, and a distance from an inner wall surface thereof to an outer circumferential surface of the adjustment unit is set so as to be in a range of 4-15 mm.

4. The injection needle described in claim 2, wherein the end face of the stabilizer unit, that contacts the skin, and the needle-protruding surface of the adjustment unit are positioned on the same plane.

5. The injection needle described in claim 1, wherein the stabilizer unit is integrally molded with the hub.

6. The injection needle described in claim 1, wherein the protruding length of the needle tube from the needle-protruding surface is 0.5-3.0 mm.

7. The injection needle described in claim 1, wherein the needle tube is in 30-33 G.

8. The injection needle described in claim 1, wherein the needle tube is tapered at least in a part thereof.

9. The injection needle described in claim 1, wherein the adjustment unit is formed in a separate unit from the needle tube and is fixed in close contact with the circumferential surface of the needle tube.

10. A drug injection device comprising:
- a needle tube of 26-33 G having a needle tip capable of sticking in a living body, the needle tip having a bevel length defined by a blade face in the needle tube extending direction;
- a hub that holds the needle tube;
- a syringe that is connected with the hub; and
- an adjustment unit provided around the needle tube and having a needle-protruding surface from which the needle tip of the needle tube protrudes, wherein the adjustment unit is formed such that a shortest distance from a circumferential edge of the needle-protruding surface to a circumferential surface of the needle tube is in a range of 0.5-1.4 mm;
- wherein a protruding length of the needle tube from the needle protruding surface is 0.9-1.4 mm, and the bevel length is 0.5-0.9 mm.

11. The drug injection device described in claim 10, further comprising:
- a stabilizer unit provided around the needle tube with a predetermined interval from the adjustment unit and having an end face that contacts a skin when sticking the needle tube in a living body.

12. The drug injection device described in claim 11, wherein the stabilizer unit is fixed to the syringe.

13. The drug injection device described in claim 11, wherein the stabilizer unit is fixed to the hub.

* * * * *